US010617866B2

(12) United States Patent
Pitts et al.

(10) Patent No.: US 10,617,866 B2
(45) Date of Patent: *Apr. 14, 2020

(54) REMINERALISATION OF CALCIFIED TISSUE

(71) Applicant: Reminova Ltd., Perth (GB)

(72) Inventors: Nigel Pitts, Dundee (GB); Christopher Longbottom, Dundee (GB); Joseph Crayston, Fife (GB); Dmitri Grinev, Dundee (GB); Iain McEwing Young, Dundee (GB)

(73) Assignee: Reminova Ltd., Perth (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/009,395

(22) Filed: Jun. 15, 2018

(65) Prior Publication Data

US 2018/0289957 A1    Oct. 11, 2018

Related U.S. Application Data

(63) Continuation of application No. 16/009,363, filed on Jun. 15, 2018, now abandoned, which is a (Continued)

(30) Foreign Application Priority Data

Apr. 21, 2008 (GB) .................................. 0807224.1

(51) Int. Cl.
| | | |
|---|---|---|
| *A61N 1/32* | (2006.01) |
| *A61K 6/06* | (2006.01) |
| *A61K 6/033* | (2006.01) |
| *A61K 8/21* | (2006.01) |
| *A61K 8/24* | (2006.01) |
| *A61K 8/64* | (2006.01) |
| *A61K 33/06* | (2006.01) |
| *A61K 33/42* | (2006.01) |
| *A61K 41/00* | (2020.01) |
| *A61L 27/12* | (2006.01) |
| *A61L 27/22* | (2006.01) |
| *A61Q 11/00* | (2006.01) |
| *A61C 19/06* | (2006.01) |
| *A61K 8/19* | (2006.01) |
| *A61N 1/05* | (2006.01) |
| *A61K 6/00* | (2020.01) |
| *C08L 1/28* | (2006.01) |
| *C08L 29/04* | (2006.01) |
| *C08L 29/14* | (2006.01) |
| *C08L 31/04* | (2006.01) |

(Continued)

(52) U.S. Cl.
CPC ............ *A61N 1/325* (2013.01); *A61C 19/063* (2013.01); *A61C 19/066* (2013.01); *A61K 6/0017* (2013.01); *A61K 6/033* (2013.01); *A61K 6/0643* (2013.01); *A61K 8/19* (2013.01); *A61K 8/21* (2013.01); *A61K 8/24* (2013.01); *A61K 8/64* (2013.01); *A61K 33/06* (2013.01); *A61K 33/42* (2013.01); *A61K 41/0047* (2013.01); *A61L 27/12* (2013.01); *A61L 27/22* (2013.01); *A61N 1/0548* (2013.01); *A61Q 11/00* (2013.01); *C08L 1/284* (2013.01); *C08L 29/04* (2013.01); *C08L 29/14* (2013.01); *C08L 31/04* (2013.01); *C08L 33/14* (2013.01); *C08L 71/02* (2013.01); *C08L 89/005* (2013.01); *A61K 2300/00* (2013.01); *A61K 2800/83* (2013.01)

(58) Field of Classification Search
CPC ....... A61N 1/325; A61N 1/0548; C08L 29/04; C08L 1/284; C08L 89/005; C08L 29/14; C08L 31/04; C08L 33/14; C08L 71/02; A61C 19/063; A61C 19/066; A61Q 11/00; A61K 41/0047; A61K 33/42; A61K 2300/00; A61K 2800/83; A61K 6/0017; A61K 8/19; A61K 6/0643; A61K 6/033; A61K 8/21; A61K 8/24; A61K 8/64; A61K 33/06; A61L 27/22; A61L 27/12

See application file for complete search history.

(56) References Cited

U.S. PATENT DOCUMENTS

| | | | | |
|---|---|---|---|---|
| 4,060,600 A | * | 11/1977 | Vit ........................... A61K 8/20 424/53 |
| 4,149,533 A | * | 4/1979 | Ishikawa ................ A61C 19/06 604/20 |

(Continued)

FOREIGN PATENT DOCUMENTS

| | | |
|---|---|---|
| WO | 99/12554 A1 | 3/1999 |
| WO | 02/19941 A1 | 3/2002 |

(Continued)

OTHER PUBLICATIONS

International Search Report for PCT International Application No. PCT/GB/2009/001009, to which this application claims priority, dated Sep. 4, 2009.

(Continued)

*Primary Examiner* — Snigdha Maewall
(74) *Attorney, Agent, or Firm* — Falk Ewers; Ewers IP Law PLLC

(57) ABSTRACT

A cosmetic and/or therapeutic treatment of tissue, such as tooth, is disclosed that effects, for instance, whitening and tissue re-building through mineralisation. Further, a method of performing iontophoresis utilizing an aqueous composition of a remineralising agent to achieve mineralisation is disclosed, as well as a kit for performing the mineralization or remineralisation.

15 Claims, 3 Drawing Sheets

Related U.S. Application Data continuation of application No. 15/382,399, filed on Dec. 16, 2016, now Pat. No. 10,076,660, which is a continuation of application No. 12/668,684, filed as application No. PCT/GB2009/001009 on Apr. 21, 2009, now abandoned.

(51) Int. Cl.
*C08L 33/14* (2006.01)
*C08L 71/02* (2006.01)
*C08L 89/00* (2006.01)

(56) References Cited

U.S. PATENT DOCUMENTS

| | | | |
|---|---|---|---|
| 5,425,641 A | 6/1995 | Fischer | |
| 6,191,190 B1 | 2/2001 | Blackwell et al. | |
| 2004/0126335 A1 | 7/2004 | Faller et al. | |
| 2005/0249654 A1 | 11/2005 | Chow | |
| 2006/0135407 A1* | 6/2006 | Silcock | A23J 3/10 424/57 |
| 2007/0003905 A1 | 1/2007 | Nguyen et al. | |
| 2008/0050408 A1 | 2/2008 | Hayman et al. | |
| 2008/0193557 A1* | 8/2008 | Reynolds | A61K 8/19 424/602 |

FOREIGN PATENT DOCUMENTS

| | | |
|---|---|---|
| WO | 02/094204 A1 | 11/2002 |
| WO | 2005/062710 A2 | 7/2005 |
| WO | 2006/130913 A1 | 12/2006 |

OTHER PUBLICATIONS

Minkov et al. "The effectiveness of sodium fluoride treatment with and without iontophoresis on the reduction of hypersensitive dentin," J. Periodontol. Apr. 1975, vol. 46(4), pp. 246-249.

Brough et al. "The effectiveness of iontophoresis in reducing dentin hypersensitivity," J. Am. Dent. Assoc. Nov. 1985; vol. 111(5), pp. 761-765.

Gangarosa "Current strategies for dentist-applied treatment in the management of hypersensitive dentine," Archives of Oral Biology, Pergamon Press, Oxford, GB, vol. 39, Jan. 1, 1994.

Simone et al. "Iontophoresis: An Alternative in the Treatment of Incipient Caries?" Braz. Dent. J. (1995), vol. 6(2), pp. 123-129.

Inaba et al. "Effect of Sodium Hypochlorite Treatment on Remineralization of Human Root Dentine in vitro," Caries Research 1996, vol. 30, pp. 218-224.

\* cited by examiner

REMINERALISATION OF CALCIFIED TISSUE

CROSS-REFERENCE TO RELATED APPLICATIONS

This application is a continuation of U.S. patent application Ser. No. 16/009,363, filed Jun. 15, 2018, which is a continuation of U.S. patent application Ser. No. 15/382,399, filed Dec. 16, 2016, which is a continuation of U.S. patent application Ser. No. 12/668,684, filed May 10, 2010, which is a U.S. National Phase Application of PCT International Application No. PCT/GB2009/001009, filed Apr. 21, 2009, which claims priority to British Application GB 0807224.1, filed Apr. 21, 2008. The entire content of these applications is incorporated herein by reference.

FIELD OF THE INVENTION

The invention concerns cosmetic and therapeutic treatment of tissue, such as tooth, to effect, for instance, whitening and tissue re-building through mineralisation.

BACKGROUND OF THE INVENTION

Iontophoresis is a non-invasive method of propelling high concentrations of a charged substance, normally a medication or a bioactive agent, using a small electric charge applied to an iontophoretic chamber.

It is known to use iontophoresis in transdermal drug delivery. Also, iontophoresis is known to be used in conjunction with fluoride containing compounds to treat dentine hypersensitivity. Simone, J. L., et al, Iontophoresis: An Alternative in the Treatment of Incipient Caries? Braz. Dent. J, 1995, 6(2), 123-129 describes, inter alia, treating dental lesions iontophoretically with sodium fluoride and claimed to find good remineralisation due to the formation of calcium fluoride, though this was not validated.

CPP-ACP is a casein derived peptide, with added calcium and phosphate, specifically, casein phosphopeptide-amorphous calcium phosphate CPP-ACP acts as a calcium and phosphate reservoir.

Conventionally, CPP-ACP is delivered to a tooth surface in several vehicles, such as chewing gum, mouth wash, toothpaste and other restorative materials.

Thus, for example, International Patent Application No. WO 02/094204 describes a composition for dental restoration including a dental restorative material and an effective amount of a casein phosphopeptide-amorphous calcium phosphate (CPP-ACP) complex or casein phosphopeptide-amorphous calcium fluoride phosphate (CPP-ACFP) complex.

When used herein, the term remineralisation is used to mean mineralisation of an area to which further material is being added, whether or not there was insufficient material at the area before the treatment.

SUMMARY OF THE INVENTION

According to a first aspect of the invention, there is provided a method of remineralising tissue which comprises pre-conditioning, the tissue to remove protein and/lipids, and then applying to the tissue a remineralising agent whilst separately, sequentially or simultaneously applying iontophoresis.

Preferably, the remineralising agent is a source of phosphate, calcium and water.

Preferably, the method comprises the remineralisation of hypo-mineralised or demineralised tooth.

In one aspect, the method is a cosmetic treatment which is directed to lightening or whitening tooth.

The method may be directed to the prevention or treatment of tooth erosion.

In another aspect the method may comprise the remineralisation of bone.

Preferably, the remineralising agent comprises casein phosphopeptide-amorphous calcium phosphate (CPP-ACP).

The remineralising agent preferably contains fluoride. An example of such a remineralising agent is casein phosphopeptide-amorphous calcium fluoride phosphate (CPP-ACFP).

Preferably, the remineralising agent includes one or more remineralisation enhancers. Typically the remineralising, enhancers are sources of calcium and phosphate ions. Examples of remineralisation enhancers may include, but are not limited to Dicalcium phosphate dehydrate (DCPD), mineral brushite; Dicalcium phosphate anhydrous (DCPA), mineral monetite; Octacalcium phosphate (OCP); alpha-tricalcium phosphate (alpha-TCP); beta-tricalcium phosphate (beta-TCP); Amorphous calcium phosphate (ACP); Calcium-deficient hydroxyapatite (CDHA); Hydroxyapatite (HA or OHAp); Fluorapatite (FA or FAp); Tetracalcium phosphate (TTCP or TetCP), mineral hilgenstockite). More preferably, the remineralisation enhancer is strontium.

The remineralising agent may include at least two remineralisation enhancers wherein one of the enhancers is a source of calcium ions and the other is a source of phosphate ions. For example the remineralising agent may include a source of calcium e.g. calcium hydroxide and a source of phosphate e.g. orthophosphoric acid. The ratio of calcium:phosphate in the remineralising agent may be between 1:1 and 22:10. Preferably the ratio of calcium:phosphate is about 10:6 (i.e. 1.67), which represents the ratio of calcium to phosphate ions in calcium hydroxyapatite. Alternatively, the ratio of calcium:phosphate in the remineralising agent may be between 9:6 and 22:10. Alternatively still, the ratio of calcium:phosphate in the remineralising agent may be greater than 1:1, but less than 3:2 (i.e. 1.0 up to 1.49).

The remineralising agents may thus be selected from the following: i) Ca:P ratio=1.67: e.g. Hydroxyapatite:Fluorapatite. Ca:P ratio=1.5-2.2 (but not 1.67): e.g. Alpha-Tricalcium phosphate; Beta-Tricalcium phosphate; Amorphous calcium phosphate; Calcium deficient Hydroxyapatite; Tetracalcium phosphate, mineral hilgenstockite. iii) Ca:P ratio=1-1.49: e.g., Dicalcium phosphate dehydrate, mineral brushite; Dicalcium phosphate anhydrous, mineral monetite.

The remineralising agent may be prepared from its component parts by 'driving' in calcium ions iontophoretically (in aqueous solution) and subsequently changing the polarity of the set-up and 'drive' in phosphate ions (in aqueous solution) with a second sequence of iontophoresis—the calcium and phosphate ions would thus 'meet' within the lesion during the second sequence of iontophoresis and precipitate out as a calcium phosphate mineral (or minerals). The hydroxyl ion of the generated apatite would come from the aqueous solution. The water-soluble calcium-containing agent might be, for example, calcium hydroxide, calcium chloride, or calcium nitrate; the water-soluble phosphate-containing agent might be, for example, orthophosphoric acid ($H_3PO_4$) sodium (or potassium) hydrogen phosphate, sodium (or potassium) dihydrogen phosphate or magnesium phosphate. The calcium agent containing solution may be separate from the phosphate agent containing solution, or combined into one solution.

Thus a preferred method of the invention comprises the steps of: i) pre-conditioning the tissue to remove protein and/lipids, and ii) applying to the tissue a calcium-containing aqueous solution and/or phosphate-containing aqueous solution whilst separately, sequentially or simultaneously applying iontophoresis. Optionally after sufficient time for the ingress of a predetermined amount of calcium ions, determined (indirectly) by measurement of the amount of current discharged into the tooth, this first phase of remineralisation would be stopped and the polarity of the iontophoresis electrode at that surface would be changed to negative; the remineralising agent would be changed to an aqueous solution of orthophosphoric acid and the iontophoresis method re-applied in order to cause the ingress of phosphate ions into the tooth. The reversal of the previous iontophoresis polarity will cause the previously migrated calcium ions within the tooth to migrate towards the surface as the phosphate ions are migrating into the tooth—this combination of calcium and phosphate ions, in aqueous solution, within the tooth will result in the deposition of orthophosphates within the tooth—i.e. remineralisation. This second phase of iontophoresis will be stopped when a pre-determined level of current has been discharged into the tooth.

Thus a further preferred method of the invention comprises the steps of i) pre-conditioning the tissue to remove protein and/lipids ii) applying to the tissue a calcium-containing aqueous solution or phosphate-containing aqueous solution whilst separately, sequentially or simultaneously applying iontophoresis, and iii) either (a) applying a phosphate-containing aqueous solution where in (ii) a calcium-containing aqueous solution was applied or (b) applying a calcium-containing aqueous solution where in (ii) a phosphate-containing aqueous solution was applied whilst separately, sequentially or simultaneously applying iontophoresis.

Preferably, the pre-conditioning step is performed, with or without the application of iontophoresis, prior to application of the remineralising agent/iontophoresis.

Preferably, the pre-conditioning step comprises treatment with an acid, more preferably, phosphoric acid.

Preferably, the pre-conditioning step comprises treatment with a hypochlorite.

A preferred method of the invention involves the treatment or alleviation of dental caries and/or dental fluorosis in a mammal.

A further preferred method of the present invention comprises the remineralising of hypo-mineralised or de-mineralised (carious) dentine.

The present invention also provides a remineralising agent for use in iontophoretic remineralising treatment of tissue which has been subject to pre-conditioning to remove protein and or lipids, the remineralising agent being a source of both phosphate and calcium.

Preferably, the remineralising agent comprises casein phosphopeptide-amorphous calcium phosphate (CPP-ACP).

The present invention further provides a kit for use in iontophoretic remineralising treatment of tissue comprising a pre-conditioning agent and a remineralising agent.

Preferably, the pre-conditioning agent and the remineralising agent are present in the kit in a suitable form for application, for instance, a liquid or a gel form.

The kit may also provide an applicator for applying the or each agent to the site of treatment

MORE DETAILED DESCRIPTION OF THE INVENTION

As indicated above, the present invention provides a method of remineralising hypo-mineralised or de-mineralised tooth. However, the method may be utilised in the remineralisation of other hypo-mineralised or de-mineralised tissue, such as, bone.

A variety of remineralising agents may be used including a mixture of remineralising agents. The remineralising agent may depend upon the tissue to be treated. However, preferably, the remineralising agent is a phosphate or calcium source, preferably a source of phosphate and calcium. An especially preferred remineralising agent is casein phosphopeptide-amorphous calcium phosphate (CPP-ACP). For use in the remineralisation of tooth, the remineralising agent may be a fluoride containing agent as hereinbefore described, such as casein phosphopeptide-amorphous calcium fluoride phosphate (CPP-ACFP). Other remineralising agents may comprise calcium phosphate compounds, such as fluoroapatite, monefite, brushite, amorphous calcium phosphate, hydroxyapatite, etc. Furthermore, it may be possible to incorporate additional elements in the remineralising agent of the invention winch may enhance the remineralisation effect, such as strontium.

It will be understood by the person skilled in the art that the terms hypo-mineralised tissue and demineralised tissue are intended to include any tissue that is deficient in its level of mineralization and includes tissue, such as tooth, that is substantially or completely demineralised, e.g. as a result of the dental caries process, thus including dental caries lesions, or a result of acid erosion, thus including 'surface-softened' enamel or dentine.

The iontophoresis may comprise the application of a voltage, e.g. a fixed voltage, or a current, e.g. a fixed current. Alternatively, the iontophoresis may comprise the application of a mixture of voltage and current, for example, the combination of voltage and current may be applied in specific sequences so as to optimise remineralisation.

In addition, in the method of the invention a preconditioning step is also included prior to application of the remineralising agent/iontophoresis. The pre-conditioning step may vary but may, for example, comprise the removal of proteins and/or lipids prior to application of the remineralising agent/iontophoresis. Although a variety of pre-conditioning steps may be used, preferably, the preconditioning step comprises a variety of processes or a mixture of processes.

Any suitable protein removing agent can be used in the preconditioning step of the present invention. The agent is required to reduce the proteinaceous barrier formed over the surface to be treated, such as the pellicle over teeth or the exogenous protein within a caries lesion. The preconditioning step may optionally include the use of iontophoresis and the various preconditioning agents, e.g. protein removing agents, may be used in a variety of combinations and/or sequences. Furthermore, any of the pre-conditioning agents may be propelled into a hypo-mineralised or demineralised region, e.g. caries lesion, by iontophoresis to optimise the disruption of the protein layer and then the polarity of the iontophoresis reversed in order to aid the removal the proteinacious material from the hypo-mineralised or demineralised tissue. Examples of suitable agents include bleach, detergent, chaotropic agents such as urea, high phosphate concentrations, cocktails of proteases (e.g. endopeptidases, proteinases and exopeptidases) and any other protein solubilising, disrupting or hydrolysing agent. Examples of suitable bleaches include sodium hypochlorite, and peroxide bleaches. In a preferred embodiment, the bleach is an alkaline bleach. In a further preferred embodiment the alkaline bleach is sodium hypochlorite. The protein disrupting agent acts to solubilise and partially or wholly remove proteins from the surface of the tooth mineral, e.g. proteins of the pellicle on the tooth surface. However, preferably the preconditioning step comprises treatment with an acid, such as an organic, acid, e.g. acetic acid, an inorganic acid, e.g. phosphoric, acid, or a bleaching agent, e.g. hypochlorite, for example, sodium hypochlorite.

The remineralising agent may be applied in a variety of forms, for example, in the form of a gel or mousse. For use in the treatment of tooth other oral applications known per se may be used.

Pre-conditioning is preferably carried out not more than one minute before the application of the remineralising agent. More preferably, the remineralising agent is applied almost contemporaneously, i.e. within seconds, of the pre-conditioning.

A preferred treatment sequence involves repeated conditioning followed by remineralising, particularly in a case where the remineralising agent includes material, such as protein, which is removed in a subsequent conditioning step.

The present invention further provides a method of cosmetic treatment of tissue by application to the tissue of a remineralising agent whilst separately, sequentially or simultaneously applying iontophoresis.

It will be further understood by the person skilled in the art that the method of the invention may also be advantageous in the field of orthopaedics, for example, in the treatment of bone pathologies in mammals, i.e. human or animals, such as fractures and/or during surgery.

The present invention provides improved remineralisation of tissue. However, conventional methods of remineralisation of tooth generally comprise remineralisation of the surface tissue, i.e. remineralisation of enamel. It is a particular advantage of the present invention that the method and/or use provide for remineralisation of dentine. Dentine is the term for a hard substance which is related to bone and forms the core of the tooth in mammals and man. Dentine consists to the extent of approximately 30% of a cell-free organic base substance, in particular glycoproteins in which collagen fibres are incorporated. The inorganic constituents are predominantly hydroxyapatite, fluoroapatite and small amounts of carbonates, magnesium and trace elements.

The present invention further provides a kit for use in iontophoretic remineralising treatment of tissue comprising a pre-conditioning agent and a remineralising agent. The remineralising agent may comprise a source of calcium and phosphate ions such as defined herein.

Preferably, the pre-conditioning agent and the remineralising agent are present in the kit in a suitable form for application, for instance, a liquid or a gel form.

The kit may also provide an applicator for applying the, or each, agent to the site of treatment.

The EAER pre-treatment and iontophoresis remineralisation treatment procedure is implemented with the aid of a kit comprising several or all of the following: (1) the EAER remineralisation smart applicator pen; (2) battery pack and/or optional mains supply/recharger; (3) a set of disposable pre-treatment electrode pads which attach to the electrode of the EAER pen; (4) bottle of hypochlorite pre-treatment hydrogel, paste or liquid; (5) a bottle of peroxide pre-treatment hydrogel, paste or liquid; (6) a set of disposable EAER remineralisation electrode pads which attach to the electrode of the EAER pen; (7) one or more bottles of hydrogel, paste or liquid containing the remineralisation agents specified above including: CPP-ACP, CPP-ACPF, etc; (8) all necessary wiring to complete the iontophoresis circuit, including a wrist-attached or mouth-attached counter electrode; (9) full instructions. The gels complete the electrical path between the electrode pad and the tooth. Further optional add-on kits would supply dental trays, strips or holders or extension applicators.

The pre-treatment electrode pads (3) and remineralisation electrode pads (6) provide a disposable barrier between the EAER pen electrode and the gel for cross-infection control purposes, and also provide a support for the hydrogel. Alternatively, the pads could be washable and sterilisable. They would preferably be composed of electrically conductive material such as carbon-filled polymer or graphite felt, or high surface area silver/silver chloride electrodes. Alternatively, they may be thin, non-conductive, open, porous sponge-like materials such as silicone or dried hydrogel which allow the applied hydrogel, paste or liquid to permeate throughout the material, providing an ionically conductive path to the underlying EAER pen electrode. in another embodiment the hydrogels may be applied directly to the EAER pen electrode without the use of an intervening, electrode pad (3) or (6).

To increase shelf-life, the pre-treatment gels or pastes (4) and (5) would preferably use an inorganic-based hydrogel or paste, such as inorganic gel formers tricalcium silicate, dicalcium silicate, and sodium silicate, or a non-reactive organic hydrogel such as polyvinyl acetate, polyvinyl butyral, polyvinyl alcohols, hydroxymethyl cellulose, konjac, p-HEMA (polyhydroxyethylmethacrylate) and polyoxypropylene-polyoxyethylene. Alternatively, the pre-treatment gel would be prepared immediately before application by mixing the dried or partially-dried hydrogel with the water-based pie-treatment agent. The remineralisation gels or pastes (7) may be based on organic hydrogels or pastes. The hydrogel should be non-toxic, non-irritant and easily mouldable to the tooth contour. Examples of such hydrogels are the non-reactive hydrogels mentioned above. These viscous gels would have viscosities on the order of 100,000 to 1,000,000 cp. Solutions or preparations with lower viscosities, such as aqueous solutions and glycerin-based compositions can also be used. Generally, neutral pH gels are advantageous; however, the pH is preferably optimized to allow the ionized form of the pre-treatment or remineralization agent to exist at a sufficient concentration.

The Tooth-Whitening (TW) and pre-treatment procedure is implemented with a similar kit, comprising of the above parts with the addition of: various tooth whitening agents in the form of a gel, paste or liquid substituted for, or used in addition to, the remineralisation agent (7). In addition, the EAER pen supplied would be modified with the TW (Tooth Whitening voltage modulation programme memory card and/or processor. The gels or pastes would be organic-based as outlined above.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps.

BRIEF DESCRIPTION OF THE DRAWINGS

The invention will now be described by way of examples only and with reference to the accompanying figures.

EXAMPLES

Example 1

In this experiment the current-time responses of an extracted tooth after the application of −I V at the working electrode were recorded. One electrode the shorted reference/counter electrode) was a 0.5 mm stainless steel wire inserted into the tooth root. The other electrode (the working electrode) was a Pt sheet electrode of area ca 0.25 cm$^2$ held in contact with a saline-soaked tissue pad, which in turn was held in contact with the tooth surface close to the enamel lesion.

Figure 1:
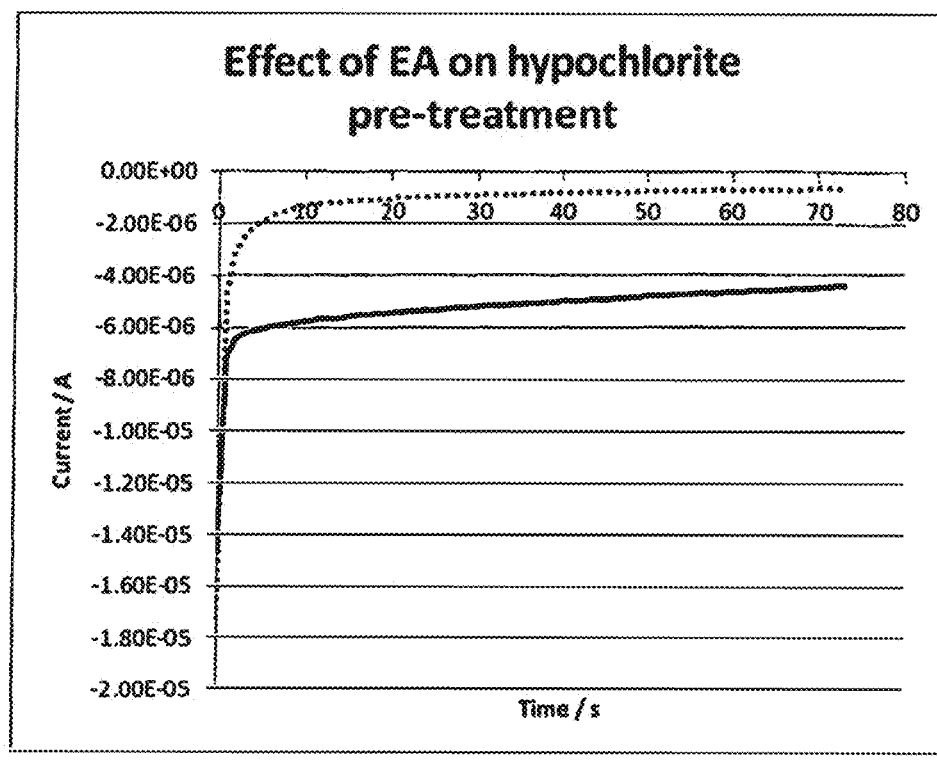
FIG. 1 is a graph showing the effect of pre-conditioning on iontophoretic treatment of a tooth. This figure shows current-time responses of a tooth obtained using a saline pad to complete the circuit between the working and reference of the counter-electrodes.

FIG. 1 shows the saline response (upper dotted line) measured after the tooth was previously held in contact with a hypochlorite-soaked pad for 3 mins. The initial current after this topical hypochlorite pre-treatment was 18 μA, over 20% higher than that of the tooth before pre-treatment, and the extended-time current was similar. The lower, solid trace shows the saline tooth response for the same tooth measured after being held in contact with a hypochlorite pad under electrically-assisted (EA) pre-treatment for 3 mins at −1 V applied at the working electrode. The initial current is similar, but the extended-time current is over five times larger (i.e. the current is more negative, being lower down the negative current scale) after EA hypochlorite pre-treatment.

Example 2

Figure 2:
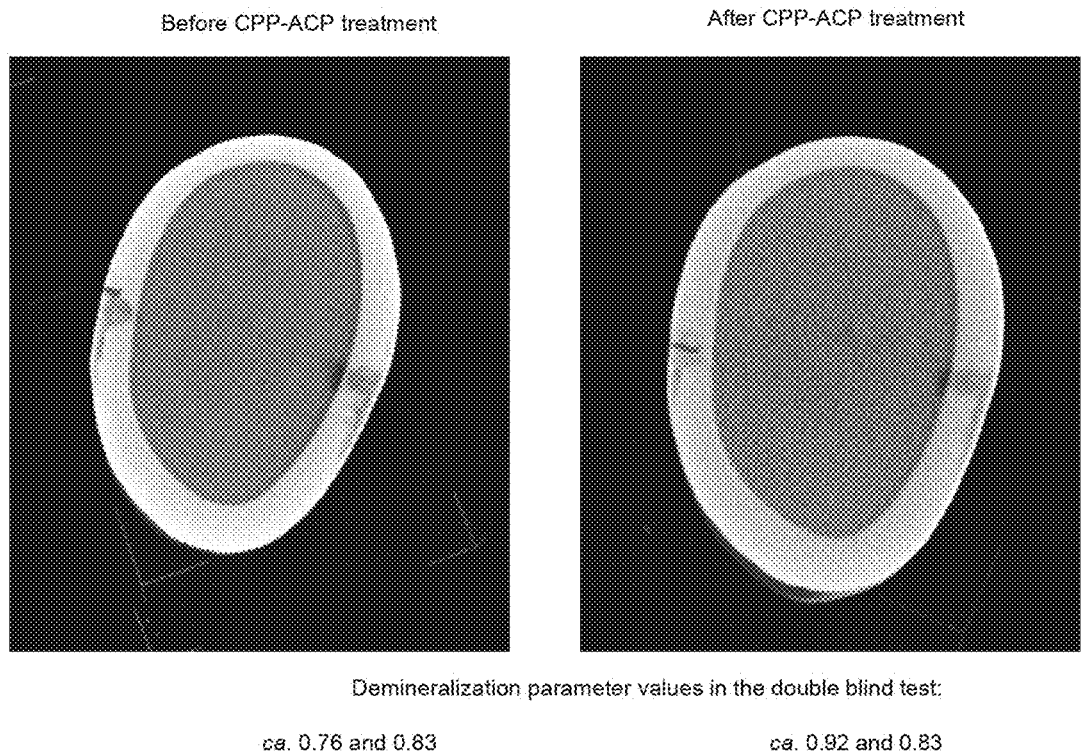
FIG. 2 shows a comparison of two lesions in one tooth before and after treatment using CPP-ACP as the remineralising agent.

FIG. 2 shows a comparison of two lesions in one tooth before and after treatment using CPP-ACP (Tooth Mousse) as the remineralising agent. Analysis of the mean mineral density of the lesions resulted in Demineralisation Parameters of 0.76 (left side) and 0.83 (right side) prior to treatment and 0.92 (left) and 0.83 (right) after treatment. This Demineralisation Parameter was derived by as comparison of average grey-scale levels within the Micro-CT image of: a) the lesion and b) the healthy tissue.

This in vitro demonstration indicates that, applying a current at a level safe and not perceived by patients at a fixed voltage to a pre-conditioned natural caries lesion, in combination with CPP-ACP in the form of Tooth Mousse resulted in significant (approximately 67%) remineralisation of the lesion (as measured by Image Analysis of Micro-CT images of the tooth before and after treatment) after 3 hours electrophoresis/iontophoresis application. The passive application of the agent Tooth Mousse-Plus (also known as MI paste) to the other natural caries lesion on the same tooth for 3 hours resulted in minimal remineralisation (measured on Micro-CT images).

The comparison in FIG. 2 is of two lesions in one tooth before and after treatment The images represent an approximately 10 micron thickness horizontal Micro-CT (XCT slice) through the same path of the tooth with separate mesial and distal lesions. The XCT image on the left shows the lesions prior to any treatment. The image on the right shows the lesions after the lesions were pre-treated to remove protein and lipids. The lesion on the left was treated with CPP-ACP and iontophoresis for three hours, whilst the lesion on the right was treated only with CPP-ACP plus Fluoride (MI paste) for three hours.

Example 3

Figure 3:
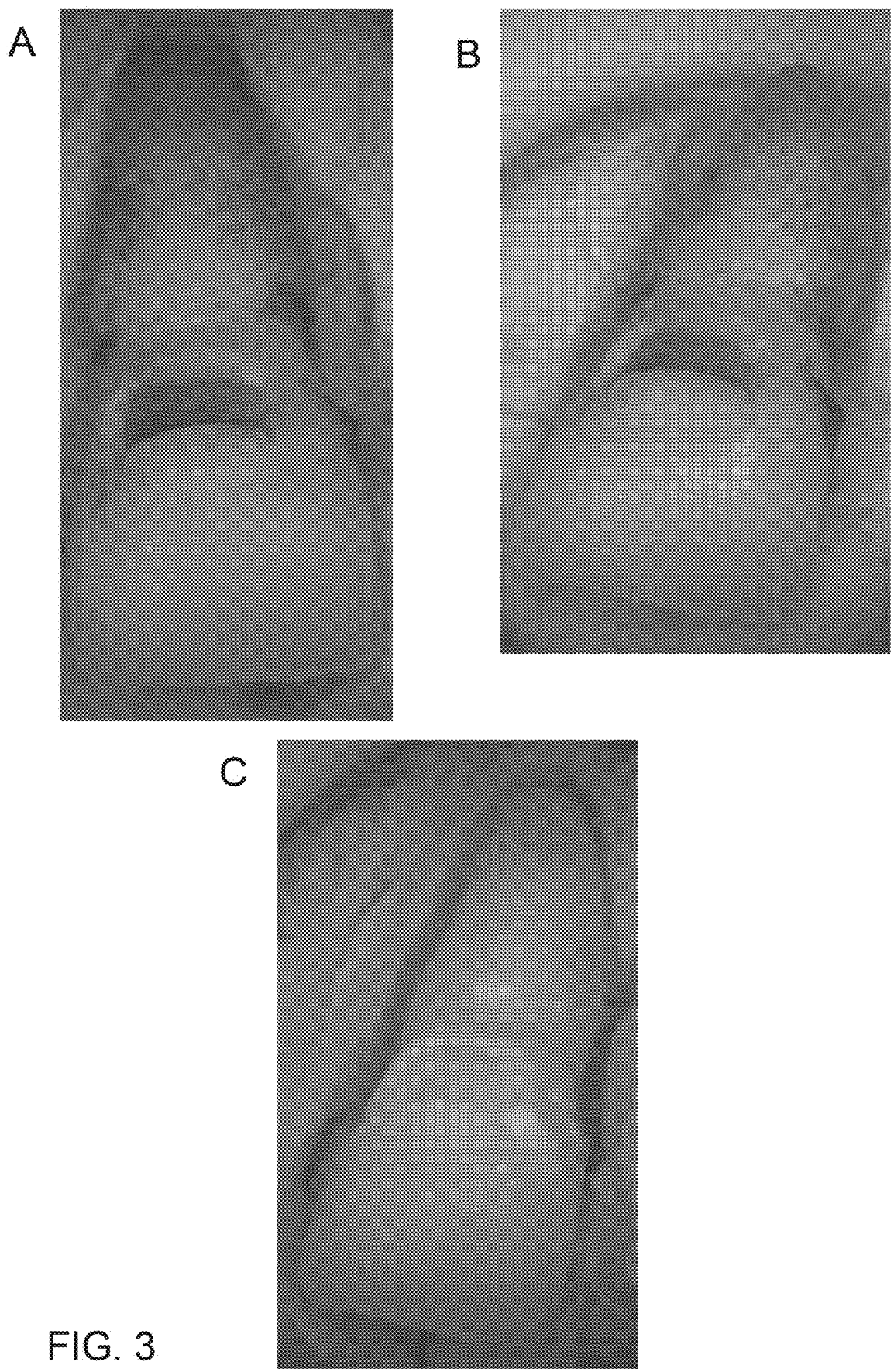
FIG. 3 shows (a) an incisor tooth before any treatment, (b) after pre-conditioning and (c) after the iontophoresis-remineralising method has been applied.

FIG. 3 shows an incisor tooth before any treatment, after pre-conditioning and after the iontophoresis-remineralising method has been applied.

The uppermost image shows an extracted incisor tooth which exhibits both a large carious cavity (caused by tooth decay), which is significantly discoloured, and areas of dark discolouration on the labial (flat) facing surface of the crown of the tooth, adjacent to the canons cavity in the direction of the incisal (lower) edge of the tooth. This image was taken prior to any treatment being carried out.

The middle image shows the same tooth after 2 minutes of pre-conditioning with sodium hypochlorite solution. There is very little difference between the uppermost and middle images in terms of tooth discolouration.

The lowermost image shows the tooth after the iontophoresis-remineralisation has been carried out using Tooth Mousse (CPP-ACP) as the re-mineralising agent for 1 hour. It is clear that the cavity has now lost its dark discolouration completely. The dark discolourations in the enamel of the crown of the tooth adjacent to the cavity have also disappeared. There is some increased whitening of the edges of the carious cavity at both the upper and lower margins of the cavity.

These images demonstrate the tooth-whitening effect of the iontophoresis-remineralising method.

The invention claimed is:

1. A method of remineralising enamel, the method comprising:
    pre-conditioning the enamel to remove protein and/or lipids;
    providing a remineralising agent including a first component and a second component;
    providing a first electrode having a first polarity;
    placing an electrode pad between the first electrode and the enamel;
    driving the remineralising agent into the enamel by applying iontophoresis with the first electrode having the first polarity for a first predetermined period of time at a constant first voltage or at a constant first current and subsequently reversing the first polarity to a second polarity and applying the iontophoresis with the first electrode having the second polarity for a second predetermined period of time at a constant second voltage or at a constant second current, or
    driving the remineralising agent into the enamel by applying iontophoresis with the first electrode having the first polarity and the second electrode having the second polarity for a third predetermined period of time at the constant third voltage or at a constant third current; and,
    depositing the remineralising agent within the enamel, wherein the remineralising agent is selected from the group consisting of casein phosphopeptide-amorphous calcium phosphate (CPP-ACP), casein phosphopeptide-amorphous calcium fluoride phosphate (CPP-ACFP), fluoroapatite, monetite, brushite, amorphous calcium phosphate, hydroxyapatite, calcium-deficient hydroxyapatite, and hilgenstockite, or a mixture thereof.

2. The method according to claim 1, wherein the electrode pad is composed of an ion-conductive material.

3. The method according to claim 1, wherein the electrode pad is composed of an electrically conductive material.

4. The method according to claim 1, wherein the electrode pad is disposable.

5. The method according to claim 1, further comprising: providing the remineralising agent as a gel or a mousse.

6. The method according to claim 1, further comprising: applying the remineralisation agent onto the electrode pad.

7. The method according to claim 1, further comprising: remineralisation of a hypo-mineralised or a de-mineralised tooth.

8. The method according to claim 7, further comprising: performing a cosmetic treatment of a tooth.

9. The method according to claim 8, further comprising: performing tooth lightening or whitening.

10. The method according to claim 1, further comprising: performing a preventive treatment of tooth erosion.

11. The method according to claim 1, wherein the remineralising agent includes one or more remineralisation enhancers.

12. The method according to claim 1, wherein a ratio of calcium:phosphate in the casein phosphopeptide-amorphous calcium phosphate (CPP-ACP), the casein phosphopeptide-amorphous calcium fluoride phosphate (CPP-ACFP), and the amorphous calcium phosphate is between 1:1 and 22:10.

13. The method according to claim 11, wherein the remineralisation enhancer is strontium.

14. The method according to claim 1, wherein the pre-conditioning comprises treatment with an acid or a hypochlorite.

15. The method according to claim 1, further comprising: performing the pre-conditioning with an application of iontophoresis.

* * * * *